United States Patent [19]

Cepela

[11] Patent Number: 5,330,529
[45] Date of Patent: Jul. 19, 1994

[54] ORBITAL IMPLANT DEVICE

[76] Inventor: Mark A. Cepela, 1078 Arden Dr., Villa Hills, Ky. 41017

[21] Appl. No.: 18,712

[22] Filed: Feb. 17, 1993

[51] Int. Cl.[5] .............................................. A61F 2/14
[52] U.S. Cl. ...................................................... 623/4
[58] Field of Search ..................... 623/4, 11, 8, 16, 66

[56] References Cited

U.S. PATENT DOCUMENTS

| | | | |
|---|---|---|---|
| 3,364,501 | 1/1968 | Stafford | 623/4 |
| 3,436,763 | 4/1969 | Milauskas | |
| 4,217,889 | 8/1980 | Radovan et al. | |
| 4,428,364 | 1/1984 | Bartolo | |
| 4,574,780 | 3/1986 | Manders | |
| 4,685,447 | 8/1987 | Iversen et al. | 623/8 |
| 4,902,292 | 2/1990 | Joseph | 623/4 |
| 4,976,731 | 12/1990 | Perry | |

Primary Examiner—David Isabella
Assistant Examiner—Debra S. Brittingham
Attorney, Agent, or Firm—Wood, Herron & Evans

[57] ABSTRACT

An orbital implant device for implantation into the orbit, particularly for children. The orbital implant device comprises a substantially rigid sphere having a self-sealing infusion site, and an integral expandable balloon overlying the posterior position of the sphere which is in communication with the self-sealing infusion site to permit increasing the effective size of the orbital implant device as the child's bone structure increases in size.

18 Claims, 2 Drawing Sheets

ORBITAL IMPLANT DEVICE

FIELD OF THE INVENTION

The invention relates to orbital implant devices as a support for an ocular prosthesis, and more particularly to devices adapted for orbital expansion.

BACKGROUND OF THE INVENTION

Eye replacement devices have been available for a number of years to effect functional and cosmetic improvements for the individual who has suffered the loss of an eye. Early ocular implants used in adults were spheres of glass or other inert solid material which filled the orbit, i.e., eye socket, and were then covered with a prosthesis which approximated the curvature and appearance of the human eye. The difficulty with these devices was that they could not be attached to the extraocular muscles. As a result, the prosthesis would not move with the functioning eye, and would both disconcert a person looking at the wearer and be a source of embarrassment to the wearer.

The devices were improved by providing means for attachment to the muscles in the orbit to permit movement in concert with the functioning eye and thereby approximate a more natural appearance. The procedure of attaching the implant device to the rectus muscles is complex but is nevertheless the most desirable procedure for an adult wearer of the implant device.

However, in the circumstance of a child born without an eye, or experiencing the loss of an eye, there is also the problem that the bone tissue surrounding the orbit increases in size as the child grows. An orbital implant which initially fits the child's orbit will soon become too small to stimulate further orbital growth, creating an unnatural appearance due to asymmetric bone growth and necessitating replacement of the ocular implant with a larger implant to stimulate similar bone growth around both orbits. If the implant device is attached to the eye muscles to mimic a natural appearance, a delicate operation must be performed to remove the implant device from the rectus muscles, followed by introduction of a new larger implant device which is reattached to those muscles. Depending on the child's age and stage of growth at the time of the first implant following enucleation, i.e., loss of the eye, the child may be required to undergo numerous additional operations to insert increasingly larger implants.

SUMMARY OF THE INVENTION

It has been an objective of the invention to provide an orbital implant device which expands in size to stimulate the growth of orbital bone tissue in children.

It is a further objective of the invention to provide an orbital implant device for use in a child's orbit which is attachable to the rectus muscles in the orbit.

It is yet a further objective of the invention to provide an orbital implant device for a child which does not need to be removed and replaced as the child grows.

These and other objectives and advantages of the invention are obtained by an orbital implant device comprised of a substantially rigid sphere and an expandable balloon integrally attached to the posterior portion of the rigid sphere. The balloon can be increased in size by the injection of fluid into the rigid sphere through an anterior self-sealing infusion site, the fluid entering the expandable portion via an infusion duct on an axis running from the front to the rear of the device. The device includes a circumferential ridge along the exterior of the rigid sphere, the ridge plane being substantially perpendicular to a line coincident with the infusion duct. This line is substantially parallel to the ground in an installed implant device. The ridge serves as the attachment site to accept sutures which are tied into the rectus muscles, thereby permitting the orbital implant device to move in concert with the remaining functional eye. Preferably, the ridge is reinforced with a cord-like material around which the suture is sewn. This reinforcement minimizes the prospect of sutures tearing through the ridge and breaking the connection between the implant device and the rectus muscles.

Fluid is injected into the expandable balloon by piercing the self-sealing infusion site on the anterior portion of the rigid sphere and injecting the contents of the syringe via a hollow needle into a cavity in the rigid sphere which communicates with the expandable balloon through the infusion duct formed in the rigid sphere. The anterior portion of the rigid sphere is substantially that portion which would be visible to an observer after the device is implanted. Of course, in actual use, the implanted device is covered with a contact lens-type curved prosthesis which approximates the appearance of the iris, pupil and sclera. The fluid is preferably a liquid, such as saline solution. However, the fluid may also be a gas.

This orbital implant device with an ocular prosthesis mounted over the anterior portion thus provides a relatively natural appearance and can be implanted in young children without need for removal and replacement as a child grows. Even in the unlikely instance that the expandable balloon of the implant device develops a leak and loses fluid, the rigid sphere of the implant device will still be functional and maintain a relatively natural appearance. There is no danger to the wearer in the event of a liquid fluid leak because the leaking solution is simply absorbed into the surrounding tissues. Where the fluid is a gas, the leaking material would likewise be absorbed by the tissues. Typically, a gas is not the fluid of choice because it is readily diffusible and also is more deformable than liquids.

The objects and advantages of the invention will be more readily apparent from the following detailed description and the drawings, in which—

DETAILED DESCRIPTION OF THE INVENTION

Figure 1:
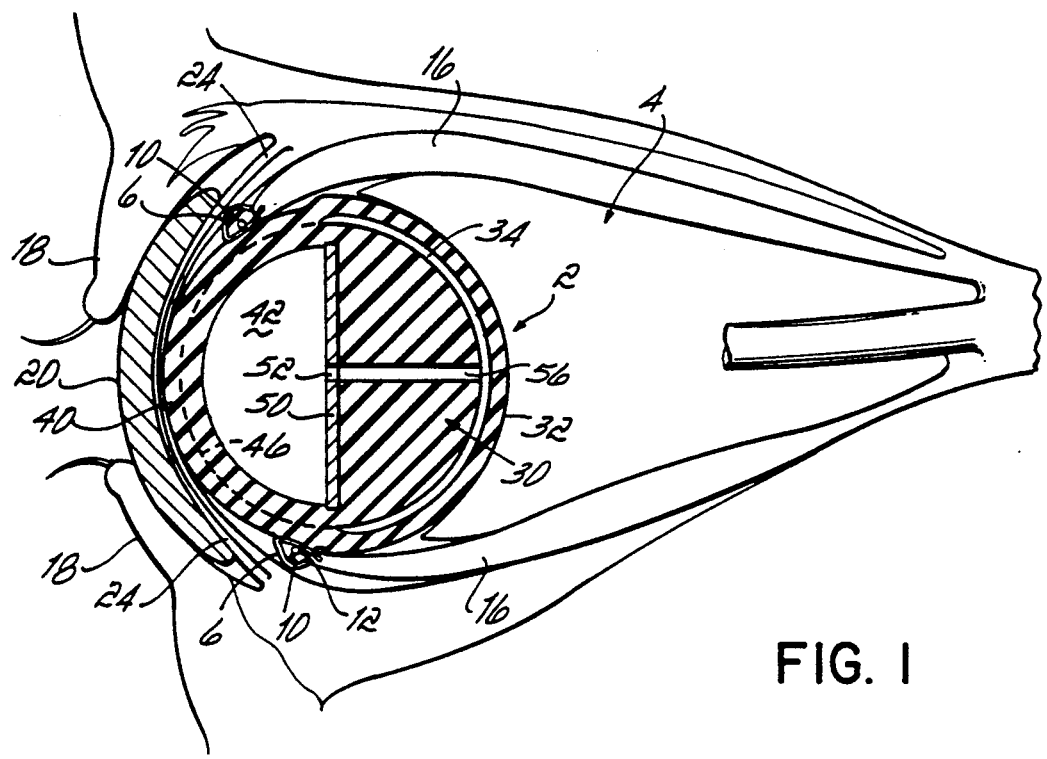
FIG. 1 is a cross-sectional view of an unexpanded orbital implant device in an orbit, with an ocular prosthesis fitted in the eye socket, anterior to the implant device.

The invention in its broader aspects relates to an orbital implant device as part of an eye prosthesis adapted for fitting into an orbit, comprising a substantially rigid sphere, inert to animal tissue, with a substantially smooth rigid exterior surface along an anterior portion of the sphere, adapted to receive a cosmetic ocular prosthesis. The device includes an expandable balloon integrally attached to and overlying the posterior portion of the sphere to define an expandable space adapted to receive a quantity of fluid, and a self-sealing infusion site on the anterior portion of the sphere which communicates with the expandable space and which is adapted to receive a hollow needle to adjust the quantity of fluid in the expandable space to thereby adjust the dimension of the balloon. The device preferably includes a circumferential ridge extending outward from the sphere for securing the orbital implant device to both surrounding tissue after implantation as well as to the rectus muscles to permit movement of the device in conjunction with the functional eye. Preferably the inert material used to form the sphere and the balloon is silicone, which will be used hereinafter to describe these components of the orbital implant device. The silicone must be inert to living animal tissue, and must be sufficiently durable to withstand years of use in the orbit. The silicone is classified as medical grade and is available from Dow Corning.

The ridge on the silicone sphere is preferably positioned just anterior to, i.e., forward of, the silicone balloon portion overlying the sphere. The positioning of the ridge in this manner approximates the normal anatomic insertion site on a functioning eye for attachment to the rectus muscles. The ridge is adapted to be pierced by a suture needle and to accept a suture to fix the rectus muscles to the implant. To further strengthen the ridge, a reinforcing component is typically incorporated into this portion of the orbital implant device. One such material is a cord made from polyethylene terephthalate, such as DACRON fiber from DuPont. Alternatively, the orbital implant device can be formed without a reinforcing ridge. Attachment of sutures would then be made directly to the anterior portion of the rigid sphere. To minimize the risks of leakage by insertion of the suture needle, the orbital implant device without a reinforcing ridge should have a thicker anterior portion for accepting sutures.

The orbital implant device preferably employs a reinforcing member, such as a metal plate, which is positioned inside the silicone sphere with its periphery contacting an inside circumference of the silicone sphere. Preferably, the metal plate is located along the major diameter of the silicone sphere, and the periphery of the metal plate contacts the silicone sphere internally along essentially an entire inside circumference of the sphere. The reinforcing member has an opening therein which is one terminus of the infusion duct, the opening preferably being in a centered location, which permits communication between a cavity behind the infusion site at the anterior portion of the sphere with the expandable balloon portion of the orbital implant device. The metal plate is used as a backstop to the cavity. This plate allows the medical personnel to better position the injection needle into the cavity behind the infusion site during insertion of the needle and also protects against inadvertent puncture of the posterior silicone balloon by the injection needle were the needle to be inserted at a wrong angle, or too deeply. To assist in improving the rigidity of silicone sphere, that portion of the silicone sphere which is posterior to the reinforcing member is also substantially solid.

Referring to the drawings, FIG. 1 shows a cross-sectional view of the orbit 4 with an unexpanded orbital implant device 2 positioned therein. The orbital implant device 2 is held in place inside the orbit 4 by sutures 6 connecting the reinforcing ridge 10 and the reinforcing cord 12 to the rectus muscles 16 within the orbit 4. As the figure shows, the sutures 6 each encircle the reinforcing cord 12 inside the reinforcing ridge 10. The attachment of the rectus muscles 16 to the orbital implant device 2 results in increased implant device movement, mimicking the motion of the remaining natural eye.

To improve the appearance of the orbital implant device 2 inside the orbit 4, an ocular prosthesis 20 approximating the visible portion of a functioning eye is inserted over the orbital implant device 2 and held in place by a friction fit. The lids 18 also function to hold the ocular prosthesis 20 in place. Between the ocular prosthesis 20 and orbital implant device 2 are the conjunctiva and Tenon's layers 24 and 25.

Figure 2:
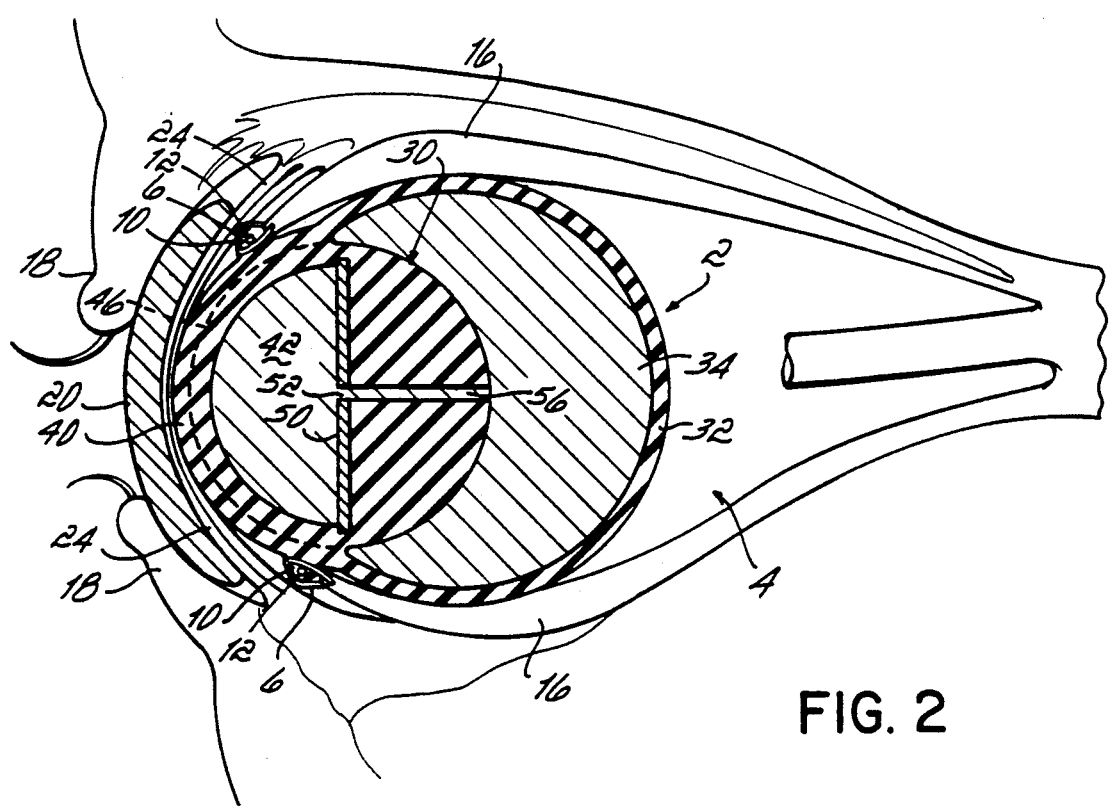
FIG. 2 is cross-sectional view of an expanded orbital implant device in an orbit, with an ocular prosthesis fitted in the eye socket, anterior to the implant device.

FIG. 2 depicts the orbital implant device 2 in the expanded state in the orbit 4 after injection of fluid.

Figure 3:
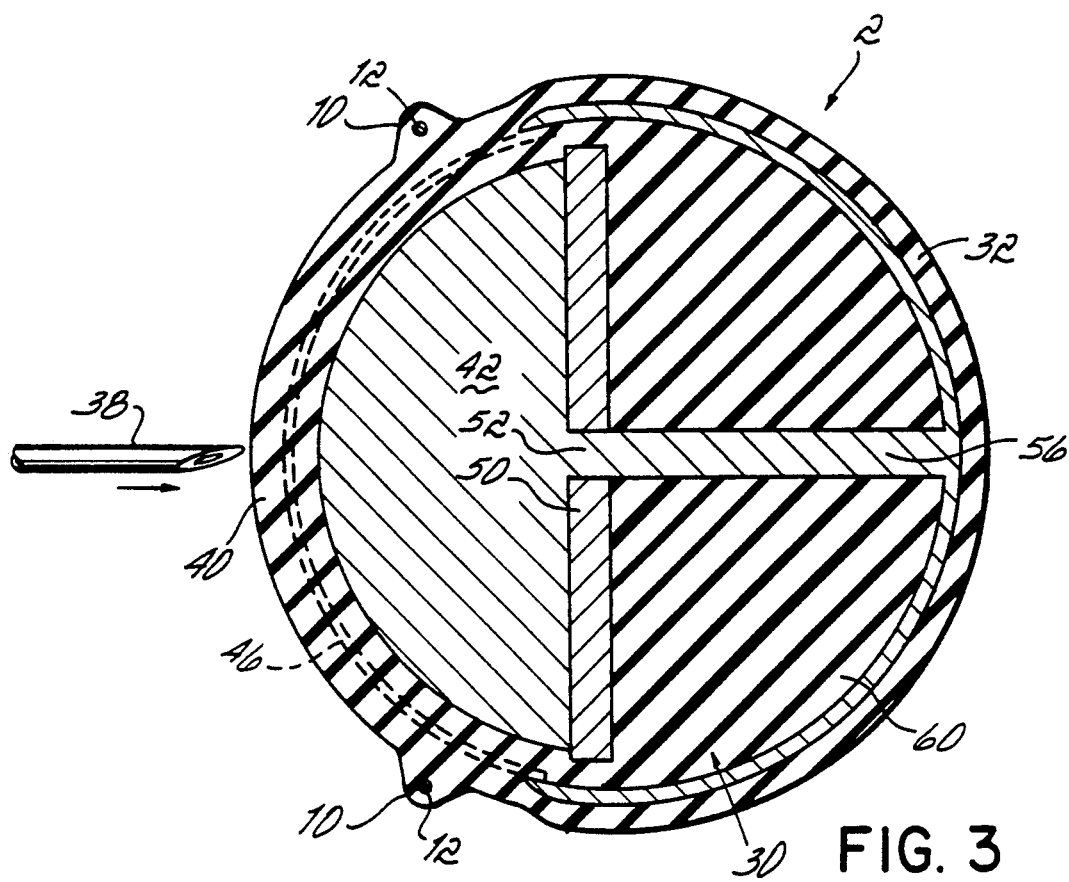
FIG. 3 is an enlarged cross-sectional view of an unexpanded orbital implant device immediately prior to insertion of a hollow needle for adjusting the fluid level inside the implant device.
Figure 4:
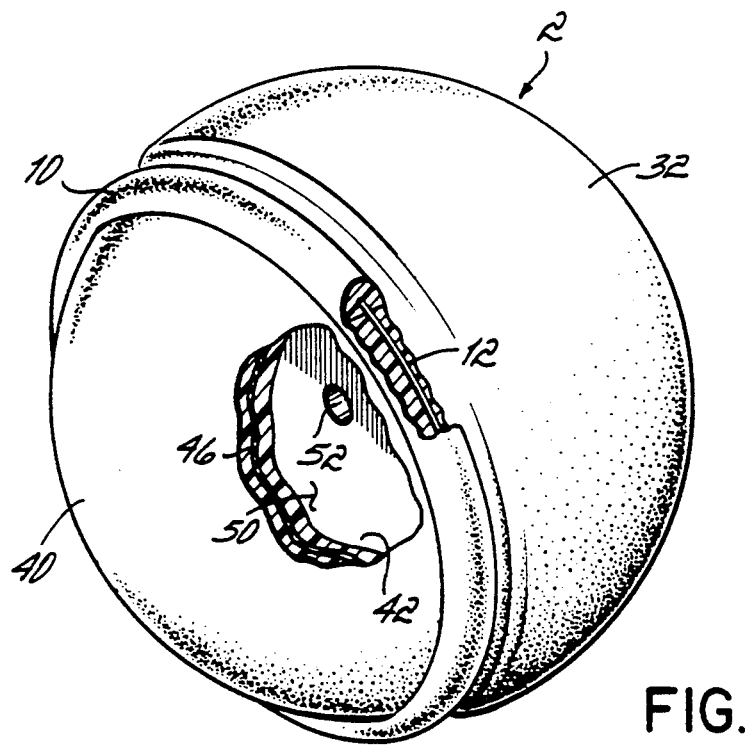
FIG. 4 is a perspective view of an orbital implant device.

FIG. 3 depicts in cross-section the orbital implant device 2 having reinforcing ridge 10, substantially rigid silicone sphere 30, and integral balloon layer 32 which defines the expandable space 34. To adjust the size of the orbital implant device 2, a piercing device such as a hollow needle 38 is inserted through the self-sealing infusion site 40 on the anterior portion of the orbital implant device 2 until the tip of the needle 38 is positioned inside the cavity 42 of the rigid silicone sphere 30. The rigidity of the self-sealing infusion site 40 is improved by the inclusion of a reinforcing mesh 46 embedded in the anterior portion of the rigid silicone sphere 30 so that little or none of the cavity 42 can be penetrated by the needle 38 without the needle 38 also passing through the reinforcing mesh 46. The reinforcing mesh 46 is manufactured from a polymeric fiber, such as polyethylene terephthalate, and reinforces the contour of the anterior portion of the orbital implant. The self-sealing infusion site 40 is sufficiently rigid that it will not change contour with injection of additional saline solution to maintain the fitting of the prosthesis 20 onto the orbital implant device 2.

Inside the rigid silicone sphere 30 is a reinforcement member 50 made from metal useful in implant applications, such as titanium. The reinforcement member 50 is approximately one millimeter thick, with a center hole 52 of about one millimeter diameter which is the terminus of the infusion duct 56 formed in the otherwise solid posterior portion 60 of the rigid silicone sphere 30, behind the reinforcement member 50. The metal is preferably non-magnetic so that it causes minimum interference with magnetic resonance imaging.

The infusion duct 56 communicates between the cavity 42 and expandable space 34. Insertion of the hollow needle 38 and introduction of fluid, typically saline solution, into the cavity 42 results in fluid flow into the expandable space 34 because of its increased resilience relative to the infusion site 40 of the rigid silicone sphere 30.

The size of the orbital implant device 2 is selected so that the orbit 4 is initially substantially filled by the orbital implant device 2 in its unexpanded state. This allows for maximum utility of the orbital implant device as the wearer ages and the orbit 4 increases in size. The orbital implant device 2 in its unexpanded condition would be produced having diameters in the range of about 12 millimeters to about 20 millimeters. After maximum expansion, the orbital implant device would be approximately 22 to 26 millimeters along the longest diameter of the orbital implant device, i.e., from the anterior measured along the anterior-posterior axis. As noted previously, the orbital implant device 2 is preferably manufactured from medical grade silicone which is inert to the tissue and which is resistant to degradation over time in contact with the surrounding tissue and fluids. This is the same material that is now used to make non-expandable orbital implants. The self-sealing infusion site 40 on the orbital implant device 2 is likewise manufactured of medical grade silicone and has a thickness of approximately 2 mm. The reinforcing mesh 46, such as is made from DACRON polyester, permits penetration by a piercing device such as the hollow needle 38. However, the mesh 46 maintains its reinforcing function embedded within the self-sealing infusion port 40. The needle 38 used to pierce the self-sealing infusion port 40 is of standard construction, typically about ⅝ inch (about 16 cm) long and 25 gauge, to cause penetration into the cavity 42 without unduly increasing the risk of the needle penetrating through to the integral balloon layer 32 which could result in leakage.

After implantation of the orbital implant device 2, and positioning of the ocular prosthesis 20 over the anterior portion thereof, there is no further reason for adjusting the diameter of the orbital implant device 2 until necessitated by growth of the wearer with consequent need to increase the size of the orbit 4. The orbital implant device 2 prior to implantation has no liquid fluid inside. After the orbital implant device 2 is filled to the required level with liquid fluid, such as saline solution. The filling procedure involves placing the patient on a flat surface, face up, and injecting the proper amount of saline solution via needle through the infusion port. Any pocket of air is bled from the implant device 2 by extraction using a hollow needle.

The orbital implant device 2 has the advantage of being functional throughout the life span of the patient and can be modified in size by adjusting the amount of fluid in the orbital implant device over its lifetime. However, even if there is some leakage of solution from the orbital implant device 2, the rigid silicone sphere 30 will maintain its shape and delay the need for replacement of the leaking orbital implant device 2. Though the implant device 2 has particular utility for use with children whose bone structure is still increasing, the orbital implant device 2 also would have utility with adults.

Thus it is apparent that there has been provided, in accordance with the invention, an orbital implant device that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the sphere and broad scope of the appended claims.

What is claimed is:

1. An orbital implant device for an eye prosthesis adapted for fitting into an orbit comprising:
   a substantially rigid sphere with a substantially smooth exterior surface along at least an anterior portion thereof adapted to receive a cosmetic eye appliance;
   an expandable balloon integrally attached to and overlying a posterior portion of said substantially rigid sphere to define an expandable space adapted to receive a quantity of fluid; and
   a self-sealing infusion site on said anterior portion of said substantially rigid sphere which communicates with said expandable space and which is adapted to receive a hollow needle to adjust said quantity of said fluid in said expandable space to thereby adjust a dimension of said expandable balloon.

2. The orbital implant device of claim 1, further including a circumferential ridge extending outwardly from said substantially rigid sphere for securing said orbital implant device in said orbit.

3. The orbital implant device of claim 2 wherein said circumferential ridge is positioned on said anterior portion of said sphere.

4. The orbital implant device of claim 1 wherein said sphere is formed from silicone.

5. The orbital implant device of claim 1 wherein said expandable balloon integrally attached to said substantially rigid sphere is formed from silicone.

6. The orbital implant device of claim 1, said self-sealing infusion site further comprising a reinforcing mesh.

7. The orbital implant device of claim 2, said circumferential ridge corresponding to anatomic insertion sites of the rectus muscles.

8. The orbital implant device of claim 2, said circumferential ridge further comprising a reinforcing component.

9. The orbital implant device of claim 8, said reinforcing component comprised of a polymeric fabric cord.

10. The orbital implant device of claim 9, said polymeric fabric cord comprised of polyethylene terephthalate.

11. An orbital implant device for an eye prosthesis adapted for fitting into an orbit comprising;
    a substantially rigid sphere with a substantially smooth exterior surface along at least an anterior portion thereof adapted to receive a cosmetic eye appliance;
    an expandable balloon integrally attached to and overlying a posterior portion of said substantially rigid sphere to define an expandable space adapted to receive a quantity of fluid;
    a circumferential ridge extending outwardly from said substantially rigid sphere for securing said orbital implant device in said orbit; and
    a self-sealing infusion site on said anterior portion of said substantially rigid sphere which communicates with said expandable space and which is adapted to receive a hollow needle to adjust said quantity of said fluid in said expandable space to thereby adjust a dimension of said expandable balloon.

12. The orbital implant device of claim 11, said circumferential ridge further comprising a reinforcing component.

13. The orbital implant device of claim 12, said reinforcing component comprised of a polymeric fabric cord.

14. The orbital implant device of claim 11, said self-sealing infusion site further comprising a reinforcing mesh.

15. The orbital implant device of claim 14, said reinforcing mesh comprised of polyethylene terephthalate.

16. An orbital implant device for an eye prosthesis adapted for fitting into an orbit comprising;
    a substantially rigid sphere inert to animal tissue, with a substantially smooth exterior surface along at least an anterior portion thereof adapted to receive a cosmetic eye appliance;

a reinforcing ridge circumferentially located around said anterior portion of said substantially rigid sphere with at least two attachment sites thereon adapted to receive sutures for securing said orbital implant device in said orbit;

an expandable balloon integrally attached to and overlying a posterior portion of said substantially rigid sphere to define an expandable space adapted to receive a quantity of fluid;

a reinforcement member inside said sphere;

a self-sealing infusion site on said substantially rigid sphere to accept a hollow needle for injecting said quantity of fluid; and a cavity inside said substantially rigid sphere which receives said quantity of fluid from said hollow needle, said cavity communicating with said expandable space through said reinforcement member to adjust said quantity of said fluid in said expandable space to thereby adjust a dimension of said expandable balloon.

17. The orbital implant device of claim 16, wherein said reinforcement member is a planar plate having a periphery in contact with a substantial portion of an inside diameter of said substantially rigid sphere.

18. The orbital implant device of claim 16, said cavity communicating with said expandable space by an infusion duct terminating at said reinforcement member.

* * * * *